US00PP09989P

United States Patent [19]

Laming et al.

[11] Patent Number: Plant 9,989

[45] Date of Patent: Aug. 5, 1997

[54] POINSETTIA PLANT NAMED 'FISSILVER'

[75] Inventors: Kenneth Laming, Chatelerault, France; Katharina Zerr, Simmern, Germany

[73] Assignee: Florfis AG, Binningen, Switzerland

[21] Appl. No.: 601,985

[22] Filed: Feb. 15, 1996

[30] Foreign Application Priority Data

Feb. 15, 1995 [DE] Germany ..... EUP 180

[51] Int. Cl.[6] ..... A01H 5/00

[52] U.S. Cl. ..... Plt./86.1

[58] Field of Search ..... Plt./86.1

*Primary Examiner*—James R. Feyrer

*Attorney, Agent, or Firm*—Foley & Lardner

[57] ABSTRACT

A new and distinct cultivar of poinsettia plant named Fissilver, characterized by its bright red bract color, light green leaves with narrow white margins, medium early flower response, and low, compact and bushy plant habit.

1 Drawing Sheet

The present invention relates to a new and distinct cultivar of Poinsettia plant known by the cultivar name Fissilver, and botanically known as *Euphorbia pulcherrima*.

The new cultivar is a naturally occurring mutation of Peterstar, disclosed in U.S. Plant Pat. No. 8,259 and characterized by its bright red bract color, medium green foliage, and its medium tall, compact and bushy habit.

The new cultivar was discovered by inventor Kenneth Laming, as a mutation among a group of young plants of the parent cultivar growing in a greenhouse in Chatellerault, France, in summer 1993. One plant had completely undergone mutation and showed variegated leaves with light green main color and white margin, in contrast to the uniform bright green foliage color of Peterstar. Since the plant looked attractive it was taken to Hillscheid, Germany, for further examination.

In spring 1994, the plant was propagated by cuttings by or under the supervision of inventor Katharina Zerr in Hillscheid, Germany. The propagated plants were observed for uniformity and stability of the foliage characteristics, and for growth characteristics as well. Since presence or absence of leaf variegation is clearly visible at any time, there was no difficulty in building up a uniform clone and keeping it true to type.

Horticultural examination initiated in Hillscheid, Germany, in 1994 and continuing thereafter has demonstrated that the combination of characteristics as herein disclosed for Fissilver are firmly fixed and are retained through successive generations of asexual reproduction.

The following traits have been repeatedly observed and are determined to be basic characteristics of Fissilver which in combination distinguish this poinsettia as a new and distinct cultivar:

1. Bright red bract color.
2. Ovate bracts are borne horizontally, with no tendency to drooping.
3. Light green leaves with narrow white margins.
4. Medium early flower response.
5. Low, compact and bushy plant habit.
6. Good keeping quality of leaves and bracts.

Fissilver has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

The plants described were potted as rooted cuttings in 12 cm pots on August 24, pinched 14 days later and grown at about 20° C. day and night temperature under natural day light conditions in Autumn. Observations and measurements were taken mainly at the beginning of flowering.

Of the many commercial cultivars known to the inventor, the most similar in comparison to Fissilver is the parent variety Peterstar. In comparison to Peterstar, Fissilver has a similar bract color and flower response time, but has variegated foliage with a light green, somewhat marbled main color and narrow white margin. Due to the partial chlorophyll deficiency, Fissilver grows more slowly and plants of Fissilver are smaller than those of Peterstar when grown under the same culture regime. In addition, the bracts and leaves of Fissilver are smaller and usually show a higher degree of lobing and rugosity. The differences in bract and leaf size are best visible or most distinct in early culture under high light intensity and diminish in autumn under low light and short day conditions.

The accompanying color photographic drawing shows typical inflorescence and foliage of Fissilver, with colors being as true as possible with illustrations of this type. The photograph is a side elevational view of a typical mature potted plant.

In the following description, color references are made to The Royal Horticultural Society Colour Chart. The color values were determined indoors in a north light.

Classification:

*Botanical.*—*Euphorbia pulcherrima.*

*Commercial.*—Poinsettia, cv. Silverstar.

Parentage: A naturally occurring mutation of Peterstar.

Plant description:

*Form.*—Compact and bushy, well branched.

*Growth habit.*—Weak to medium growth. Height (above soil line):16.5 cm. Diameter/width: 33.0 cm. Average no. of branches: 6.5.

*Rooting.*—Fast, less than 20 days.

*Blooming habit.*—Under natural short day conditions in late November; plant is saleable a few days before cyathia open. Response time is about 9 weeks.

*Foliage.*—Size: Leaf blade: Length: 9.0 cm. Width: 7.5 cm. Petiole: 5.0 cm. Color: Light green main color, slightly marbled with lighter green spots; narrow, irregularly shaped white margin. Upper Surface: Main color 138 A, with lighter spots of 191 A; white margin 155 A. Under Surface: Approximately 138 A-B, with white margin 155 A. Leaf petiole and basal part of midrib: dark red, about 178 B. Shape:

Ovate, almost straight or slightly rounded base and acuminate apex. Texture: Upper surface: glabrous, slightly rugose; Under surface: weak veins. Edge of Margin: Mainly entire, partly with irregular crenation. occasionally small pointed lobes.

Flowering description:

*Cyathia.*—Few (10–14) in a narrow cluster, light green, medium size.

*Bracts.*—Shape: Ovate to broad elliptical, with acuminate apex and rounded or slightly wedge-shaped base, margin entire, occasionally weak lobes. Texture: Upper surface weakly rugose, lower surface has light/whitish veins. Size: Largest bract is 9.5–10.0 cm long, including petiole. Aspect: Horizontally or somewhat upward, slightly folded. Color: Bright red, upper surface 46 B-C. lower surface 46 C-D.

Reproductive organs:

*Nectar cups.*—1–2 per cyathium, orange-yellow, often infused with red.

*Stamens.*—Red, changing to brown, abortive.

*Pollen.*—Hardly any pollen.

*Styles.*—Dark red.

*Ovaries.*—Light green, top light red; triangular, 3-celled, 3 ovules.

It is claimed:

1. A new and distinct cultivar of poinsettia plant named Fissilver, as illustrated and described.

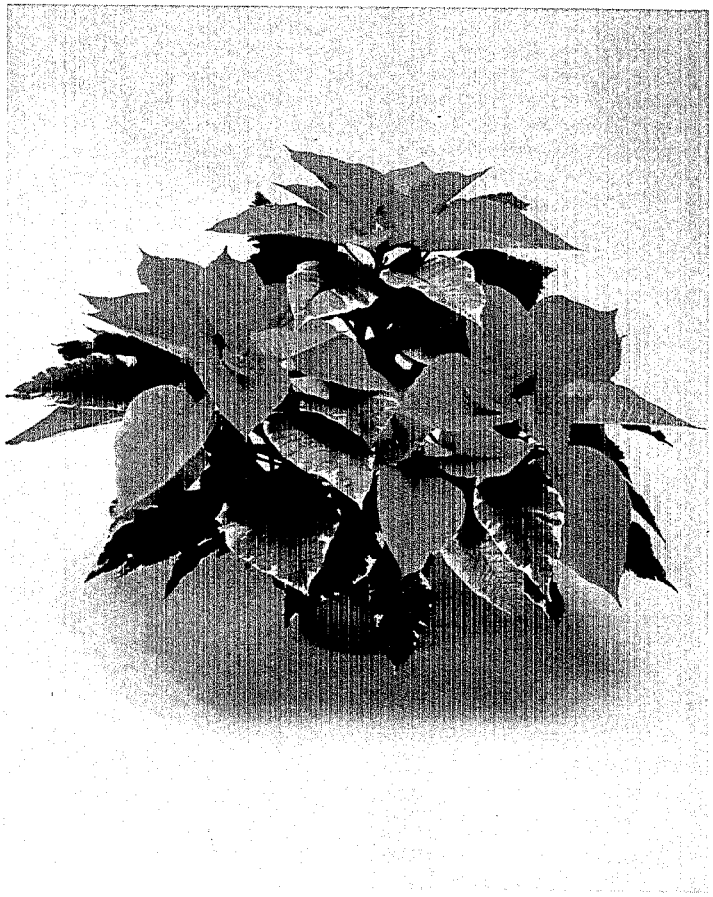

* * * * *